(12) United States Patent
Smith et al.

(10) Patent No.: US 9,249,176 B2
(45) Date of Patent: Feb. 2, 2016

(54) 4'-AZIDO, 3'-DEOXY-3'-FLUORO SUBSTITUTED NUCLEOSIDE DERIVATIVES AS INHIBITORS OF HCV RNA REPLICATION

(71) Applicant: Riboscience LLC, Palo Alto, CA (US)

(72) Inventors: Mark Smith, San Francisco, CA (US); Klaus G. Klumpp, West Chester, PA (US)

(73) Assignee: Riboscience LLC, Palo Alto, CA (US)

( * ) Notice: Subject to any disclaimer, the term of this patent is extended or adjusted under 35 U.S.C. 154(b) by 0 days.

(21) Appl. No.: 14/279,188

(22) Filed: May 15, 2014

(65) Prior Publication Data

US 2014/0341848 A1     Nov. 20, 2014

Related U.S. Application Data

(60) Provisional application No. 61/824,034, filed on May 16, 2013.

(51) Int. Cl.
| | | |
|---|---|---|
| C07H 19/10 | (2006.01) | |
| C07H 19/20 | (2006.01) | |
| A61K 31/7068 | (2006.01) | |
| A61K 45/06 | (2006.01) | |
| A61K 31/7072 | (2006.01) | |

(52) U.S. Cl.
CPC ............ *C07H 19/10* (2013.01); *A61K 31/7068* (2013.01); *A61K 31/7072* (2013.01); *A61K 45/06* (2013.01); *C07H 19/20* (2013.01)

(58) Field of Classification Search
None
See application file for complete search history.

(56) References Cited

U.S. PATENT DOCUMENTS

| | | |
|---|---|---|
| 4,147,864 A | 4/1979 | Woodward et al. |
| 5,449,664 A | 9/1995 | Verheyden et al. |
| 5,807,876 A | 9/1998 | Armistead et al. |
| 6,054,472 A | 4/2000 | Armistead et al. |
| 6,344,465 B1 | 2/2002 | Armistead et al. |
| 6,498,178 B2 | 12/2002 | Stamos et al. |
| 6,784,166 B2 | 8/2004 | Devos et al. |
| 2004/0259934 A1 | 12/2004 | Olsen et al. |
| 2007/0042988 A1 | 2/2007 | Klumpp et al. |
| 2013/0281686 A1 | 10/2013 | Cho et al. |

FOREIGN PATENT DOCUMENTS

| | | |
|---|---|---|
| BE | 875247 A | 10/1979 |
| DE | 2506330 A1 | 9/1975 |
| WO | 8606380 A1 | 11/1986 |
| WO | 9740028 A1 | 10/1997 |
| WO | 9817679 A1 | 4/1998 |
| WO | 9822496 A2 | 5/1998 |
| WO | 9840381 A1 | 9/1998 |
| WO | 9901582 A1 | 1/1999 |
| WO | 9907734 A2 | 2/1999 |
| WO | 0006529 A1 | 2/2000 |
| WO | 0009543 A2 | 2/2000 |
| WO | 0010573 A1 | 3/2000 |
| WO | 0013708 A1 | 3/2000 |
| WO | 0018231 A1 | 4/2000 |
| WO | 0056331 A1 | 9/2000 |
| WO | 0132153 A2 | 5/2001 |
| WO | 0185172 A1 | 11/2001 |
| WO | 0204425 A2 | 1/2002 |
| WO | 0218369 A1 | 3/2002 |
| WO | 02100415 A2 | 12/2002 |
| WO | 02100846 A1 | 12/2002 |
| WO | 02100851 A2 | 12/2002 |
| WO | 03007945 A1 | 1/2003 |
| WO | 03010141 A2 | 2/2003 |
| WO | 03000254 A1 | 3/2003 |
| WO | 03037893 A1 | 5/2003 |
| WO | 03037894 A1 | 5/2003 |
| WO | 03037895 A1 | 5/2003 |
| WO | 2004000858 A2 | 12/2003 |
| WO | 2004014312 A2 | 2/2004 |
| WO | 2004096235 A2 | 11/2004 |
| WO | 2004099241 A1 | 11/2004 |
| WO | 2005012327 A2 | 2/2005 |

(Continued)

OTHER PUBLICATIONS

Congiatu et al., Naphthyl phosphoramidate derivatives of BVdU as potential anticancer agents: design, synthesis and biological evaluation, Nucleosides, Nucleotides, and Nucleic Acids, vol. 24(5-7), pp. 485-489, 2005.

McGuigan et al., Phosphoramidate ProTides of 2'-C-Methylguanosine as Highly Potent Inhibitors of Hepatitis C Virus. Study of Their in Vitro and in Vivo Properties, J. Med. Chem, vol. 53, pp. 4949-4957, 2010.

(Continued)

*Primary Examiner* — Traviss C McIntosh, III

(74) *Attorney, Agent, or Firm* — GrayRobinson, P.A.; Jennifer L. Kisko

(57) ABSTRACT

The present disclosure relates to the compound of Formula I:

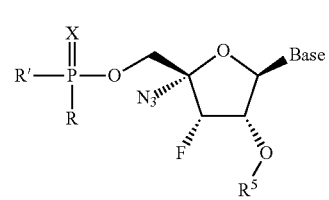

Also disclosed are pharmaceutical compositions comprising the compound of Formula I, methods of using the compound of Formula I and/or compositions comprising the compound of Formula I for the treatment of HCV.

20 Claims, No Drawings

(56) References Cited

FOREIGN PATENT DOCUMENTS

| WO | 2005073195 A2 | 8/2005 |
| WO | 2005073216 A2 | 8/2005 |
| WO | 2006063281 A2 | 6/2006 |
| WO | 2007095269 A2 | 8/2007 |
| WO | 2008017507 A2 | 2/2008 |
| WO | 2008021927 A2 | 2/2008 |
| WO | 2008085508 A2 | 7/2008 |
| WO | 2008142055 A2 | 11/2008 |
| WO | 2012040124 A1 | 3/2012 |
| WO | 2012040127 A1 | 3/2012 |
| WO | 2012048013 A2 | 4/2012 |
| WO | 2013092447 A1 | 6/2013 |
| WO | WO2013/092447 | * 6/2013 |

OTHER PUBLICATIONS

Smith et al., The Design, Synthesis, and Antiviral Activity of Monofluoro and Difluoro Analogues of 4'-Azidocytidine against Hepatitis C Virus Replication: The Discovery of 4'-Azido-2'-deoxy-2'-fluorocytidine and 4'-Azido-2'-dideoxy-2',2'-difluorocytidine, J. Med. Chem, vol. 52(9) (2009) pp. 2971-2978.

* cited by examiner

4'-AZIDO, 3'-DEOXY-3'-FLUORO SUBSTITUTED NUCLEOSIDE DERIVATIVES AS INHIBITORS OF HCV RNA REPLICATION

CROSS-REFERENCE TO RELATED APPLICATIONS

This application claims priority to U.S. provisional application Ser. No. 61/824,034, filed May 16, 2013, the disclosure of which is incorporated herein by reference and is commonly owned.

FIELD OF THE INVENTION

The invention relates to nucleoside derivatives as inhibitors of HCV replicon RNA replication. In particular, the invention is concerned with the use of purine and pyrimidine nucleoside derivatives as inhibitors of subgenomic Hepatitis C Virus (HCV) RNA replication and pharmaceutical compositions containing such compounds.

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, Sem. Liver. Dis., 1999, 19, 35). These are interferon-α monotherapy and, more recently, combination therapy of the nucleoside analogue, ribavirin (Virazole), with interferon-α.

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. This conversion to the triphosphate is commonly mediated by cellular kinases and therefore the direct evaluation of nucleosides as inhibitors of HCV replication is only conveniently carried out using a cell-based assay. For HCV the availability of a true cell-based viral replication assay or animal model of infection is lacking.

Hepatitis C virus belongs to the family of Flaviridae. It is an RNA virus, the RNA genome encoding a large polyprotein which after processing produces the necessary replication machinery to ensure synthesis of progeny RNA. It is believed that most of the non-structural proteins encoded by the HCV RNA genome are involved in RNA replication. Lohmann et al. [V. Lohmann et al., Science, 1999, 285, 110-113] have described the construction of a Human Hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

SUMMARY OF THE INVENTION

The compounds of Formula I are useful for the treatment of diseases mediated by the Hepatitis C Virus (HCV) and for pharmaceutical compositions comprising such compounds.

The application provides a compound of Formula I:

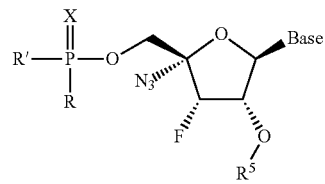

wherein:
R is O—$R^1$ or $NR^4R^{1'}$;
R' is $N(R^4)C(R^{2a})(R^{2b})C(=O)OR^3$ or —$OR^3$;
  $R^{1'}$ is —$C(R^{2a})(R^{2b})C(=O)OR^3$;
  $R^1$ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —$N(R^{1a})_2$, acylamino, —$SO_2N(R^{1a})_2$, —$COR^{1b}$, —$SO_2(R^{1c})$, —$NHSO_2(R^{1c})$, nitro or cyano;
    each $R^{1a}$ is independently H or lower alkyl;
    each $R^{1b}$ is independently —$OR^{1a}$ or —$N(R^{1a})_2$;
    each $R^{1c}$ is lower alkyl;
    each $R^{2a}$ and $R^{2b}$ are independently H, lower alkyl, —$(CH_2)_rN(R^{1a})_2$, lower hydroxyalkyl, —$CH_2SH$, —$(CH_2)S(O)_pMe$, —$(CH_2)_3NHC(=NH)NH_2$, (1H-indol-3-yl)methyl, (1H-indol-4-yl)methyl, —$(CH_2)_mC(=O)R^{1b}$, aryl and aryl lower alkyl, wherein aryl may optionally be substituted with one or more hydroxy, lower alkyl, lower alkoxy, halo, nitro or cyano;
    m is 0 to 3;
    p is 0 to 2;
    r is 1 to 6;
    or $R^{2a}$ is H and $R^{2b}$ and $R^4$ together form $(CH_2)_n$;
    n is 4 or 5;
    $R^3$ is H, lower alkyl, lower haloalkyl, phenyl or phenyl lower alkyl;
    $R^4$ is H, lower alkyl, or $R^{2b}$ and $R^4$ together form $(CH_2)_3$;
  $R^5$ is H, $C(=O)R^{1c}$, $C(=O)R^{1b}$, $P(=O)(OR^1)(OR^{1a})$, or $P(=O)(OR^1)(NR^4R^7)$;
  Base is uracil, cytosine, guanine, adenine, thymine, 7-deaza-7-fluoro adenosine or heterocycloalkyl, each of which may optionally substituted with one or more hydroxy, lower alkyl, lower alkoxy, halo, nitro or cyano; and
  X is O or S;
or a pharmacologically acceptable salt thereof.

The application provides a method for treating a Hepatitis C Virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

The compounds of Formula I have been shown to be inhibitors of subgenomic Hepatitis C Virus replication in a hepatoma cell line. These compounds have the potential to be efficacious as antiviral drugs for the treatment of HCV infections in human.

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms. Most preferred are methyl, ethyl, propyl, isopropyl, n-butyl, isobutyl, tert-butyl or pentyl. The alkyl may be unsubstituted or substituted. The substituents are selected from one or more of cycloalkyl, nitro, amino, alkyl amino, dialkyl amino, alkyl carbonyl and cycloalkyl carbonyl.

The term "cycloalkyl" as used herein denotes an optionally substituted cycloalkyl group containing 3 to 7 carbon atoms, e.g. cyclopropyl, cyclobutyl, cyclopentyl, cyclohexyl or cycloheptyl.

The term "alkoxy" as used herein denotes an optionally substituted straight or branched chain alkyl-oxy group wherein the "alkyl" portion is as defined above such as methoxy, ethoxy, n-propyloxy, i-propyloxy, n-butyloxy, i-butyloxy, tert-butyloxy, pentyloxy, hexyloxy, heptyloxy including their isomers.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert-butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes to unsubstituted or substituted hydrocarbon chain radical having from 2 to 7 carbon atoms, preferably 2 to 4 carbon atoms, and having one or where possible two triple bonds, preferably one triple bond. Examples are ethynyl, 1-propynyl, 2-propynyl, 1-butynyl, 2-butynyl or 3-butynyl.

The term "hydroxyalkyl" as used herein denotes a straight or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "alkylthio" as used herein denotes a straight or branched chain (alkyl)S-group wherein the "alkyl" portion is as defined above. Examples are methylthio, ethylthio, n-propylthio, i-propylthio, n-butylthio, i-butylthio or tert.-butylthio.

The term "aryl" as used herein denotes an optionally substituted phenyl and naphthyl (e.g. 1-naphthyl, 2-naphthyl or 3-naphthyl). Suitable substituents for aryl can be selected from those named for alkyl, in addition however, halogen, hydroxy and optionally substituted alkyl, haloalkyl, alkenyl, alkynyl and aryloxy are substituents which can be added to the selection.

The term "heterocyclyl" as used herein denotes an optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e.g. 1,2,3-triazolyl or 1,2,4-triazolyl, 1-pyrazolyl, 2-pyrazolyl, 4-pyrazolyl, piperidinyl, morpholinyl (e.g. 4-morpholinyl), thiomorpholinyl (e.g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e.g. 1,2,3-thiadiazolyl, 4-methylpiperazinyl, 4-hydroxypiperidin-1-yl.

Suitable substituents for heterocyclyl can be selected from those named for alkyl, in addition however, optionally substituted alkyl, alkenyl, alkynyl, an oxo group (=O) or aminosulphonyl are substituents which can be added to the selection.

The term "acyl" ("alkylcarbonyl") as used herein denotes a group of formula C(=O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term halogen stands for fluorine, chlorine, bromine or iodine, preferable fluorine, chlorine, bromine.

In the pictorial representation of the compounds given throughout this application, a thickened tapered line (▬) indicates a substituent which is above the plane of the ring to which the asymmetric carbon belongs and a dotted line (''''''') indicates a substituent which is below the plane of the ring to which the asymmetric carbon belongs.

Compounds of Formula I exhibit stereoisomerism. These compounds can be any isomer of the compound of Formula I or mixtures of these isomers. The compounds and intermediates of the present invention having one or more asymmetric carbon atoms may be obtained as racemic mixtures of stereoisomers which can be resolved.

Compounds of Formula I exhibit tautomerism that means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of Formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

The application provides a compound of Formula I:

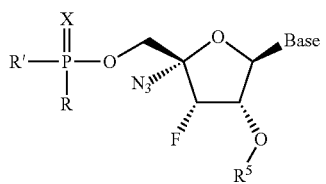

wherein:
R is O—R¹ or NR⁴R¹';
R' is N(R⁴)C(R²ᵃ)(R²ᵇ)C(=O)OR³ or —OR³;
  R¹' is —C(R²ᵃ)(R²ᵇ)C(=O)OR³;
  R¹ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —N(R¹ᵃ)₂, acylamino, —SO₂N(R¹ᵃ)₂, —COR¹ᵇ, —SO₂(R¹ᶜ), —NHSO₂(R¹ᶜ), nitro or cyano;
  each R¹ᵃ is independently H or lower alkyl;
  each R¹ᵇ is independently —OR" or —N(R¹ᵃ)₂;
  each R¹ᶜ is lower alkyl;
  each R²ᵃ and R²ᵇ are independently H, lower alkyl, —(CH₂)ᵣN(R¹ᵃ)₂, lower hydroxyalkyl, —CH₂SH, —(CH₂)ᵣS(O)ₚMe, —(CH₂)₃NHC(=NH)NH₂, (1H-indol-3-yl)methyl, (1H-indol-4-yl)methyl, —(CH₂)ₘC(=O)R¹ᵇ, aryl and aryl lower alkyl, wherein aryl may optionally be substituted with one or more hydroxy, lower alkyl, lower alkoxy, halo, nitro or cyano;
  m is 0 to 3;
  p is 0 to 2;
  r is 1 to 6;
  or R²ᵃ is H and R²ᵇ and R⁴ together form (CH₂)ₙ;
  n is 4 or 5;
  R³ is H, lower alkyl, lower haloalkyl, phenyl or phenyl lower alkyl;
  R⁴ is H, lower alkyl, or R²ᵇ and R⁴ together form (CH₂)₃;
R⁵ is H, C(=O)R¹ᶜ, C(=O)R¹ᵇ, P(=O)(OR¹)(OR¹ᵃ), or P(=O)(OR¹ᵃ)(NR⁴R⁷);
Base is uracil, cytosine, guanine, adenine, thymine, 7-deaza-7-fluoro adenosine or heterocycloalkyl, each of which may optionally substituted with one or more hydroxy, lower alkyl, lower alkoxy, halo, nitro or cyano; and
X is O or S;
or a pharmacologically acceptable salt thereof.

The application provides the above compound of Formula I, wherein R is O—R¹.

The application provides the above compound of Formula I, wherein R⁵ is H.

The application provides the above compound of Formula I, wherein R¹ is naphthyl or phenyl.

The application provides the above compound of Formula I, wherein R' is N(R⁴)C(R²ᵃ)(R²ᵇ)C(=O)OR³.

The application provides the above compound of Formula I, wherein R²ᵃ is H and R²ᵇ is methyl.

The application provides the above compound of Formula I, wherein R³ is isopropyl.

The application provides the above compound of Formula I, wherein R⁴ is H.

The application provides the above compound of Formula I, wherein Base is uracil, cytosine, guanine, adenine, thymine, or 7-deaza-7-fluoro adenosine.

The application provides the above compound of Formula I, wherein Base is uracil or cytosine.

The application provides the above compound of Formula I, X is O.

The application alternatively provides the above compound of Formula I, wherein X is S.

The application provides any of the above compounds of Formula I, wherein Base is uracil.

The application provides a compound of Formula I, selected from the group consisting of:
4'-Azido-3'-de oxy-3'-fluorouridine-5'-(O-phenyl-N—(S)-1-(isopropoxycarbonyl)ethyl thiophosphoramidate;
4'-Azido-3'-de oxy-3'-fluorouridine-5'-(O-1-naphthyl-N—(S)-1-(isopropoxycarbonyl)ethyl thiosphosphoramidate;
4'-Azido-3'-deoxy-3'-fluorouridine-5'-(O-2-naphthyl-N—(S)-1-(isopropoxycarbonyl)ethyl thiosphosphoramidate;
4'-Azido-3'-deoxy-3'-fluorocytidine-5'-(O-phenyl-N—(S)-1-(isopropoxycarbonyl)ethyl thiophosphoramidate;
4'-Azido-3'-deoxy-3'-fluorocytidine-5'-(O-2-naphthyl-N—(S)-1-(isopropoxycarbonyl)ethyl thiosphosphoramidate;
4'-Azido-3'-deoxy-3'-fluorocytidine-5'-(O-2-naphthyl-N—(S)-1-(isopropoxycarbonyl)ethyl thiosphosphoramidate;
4'-Azido-3'-deoxy-3'-fluorouridine-5'-{N,N'-bis[(S)-1-(isopropoxylcarbonyl)ethyl]phosphorodiamidate;
4'-Azido-3'-deoxy-3'-fluorocytidine-5'-{N,N'-bis[(S)-1-(isopropoxylcarbonyl)ethyl]phosphorodiamidate;
4'-Azido-3'-deoxy-3'-fluorouridine-5'-{N,N'-bis[(S)-1-(isopropoxylcarbonyl)ethyl]thiphosphorodiamidate;
4'-Azido-3'-deoxy-3'-fluorocytidine-5'-{N,N'-bis[(S)-1-(benzyloxycarbonyl)ethyl]phosphorodiamidate;
4'-Azido-3'-deoxy-3'-fluorocytidine-5'-{N,N'-bis[(S)-1-(2,2-dimethylpropyloxylcarbonyl)ethyl]phosphorodiamidate;
4'-Azido-3'-deoxy-3'-fluorocytidine-5'-{N,N'-bis[(S)-1-(3,3-dimethylbutyloxylcarbonyl)ethyl]phosphorodiamidate;
4'-Azido-3'-deoxy-3'-fluorocytidine-5'-{N,N'-bis[(S)-1-(pentyloxylcarbonyl)ethyl]phosphorodiamidate; and
4'-Azido-3'-deoxy-3'-fluorocytidine-5'-{N,N'-bis[(S)-1-(cyclopentyloxylcarbonyl)ethyl]phosphorodiamidate.

The application provides a method for treating a Hepatitis C Virus (HCV) infection comprising administering to a patient in need thereof a therapeutically effective amount of a compound of Formula I.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application alternatively provides the above method, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

The application provides the above method for inhibiting replication of HCV in a cell comprising administering a compound of Formula I.

The application provides a composition comprising the compound of Formula I.

The application provides the above composition, admixed with at least one carrier, diluent or excipient.

The application provides a use of the compound of Formula I in the manufacture of a medicament for the treatment of HCV.

The application provides a compound, composition, or method as described herein.

TABLE 1

| Compound Number | Structure | Name |
|---|---|---|
| I-1 | 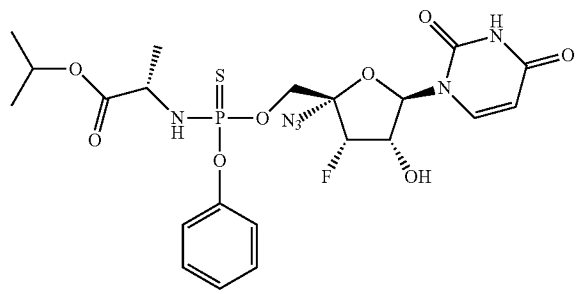 [SMILES: CC(C)OC(=O)[C@H](C)NP(=S)(OC[C@@]1(N=[N+]=[N-])O[C@@H](n2ccc(=O)[nH]c2=O)[C@H](O)[C@@H]1F)Oc1ccccc1] | 4'-Azido-3'-deoxy-3'-fluorouridine-5'-(O-phenyl-N-(S)-1-(isopropoxycarbonyl)ethyl thiophosphoramidate |
| I-2 | 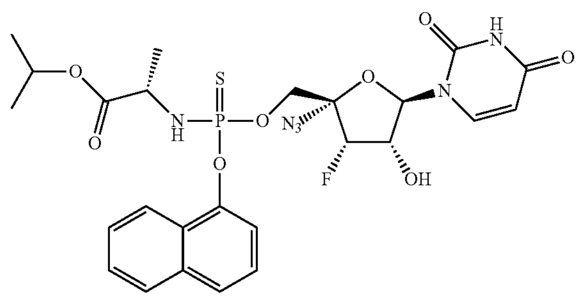 [SMILES: CC(C)OC(=O)[C@H](C)NP(=S)(OC[C@@]1(N=[N+]=[N-])O[C@@H](n2ccc(=O)[nH]c2=O)[C@H](O)[C@@H]1F)Oc1cccc2ccccc12] | 4'-Azido-3'-deoxy-3'-fluorouridine-5'-(O-1-naphthyl-N-(S)-1-(isopropoxycarbonyl)ethyl thiosphosphoramidate |
| I-3 | 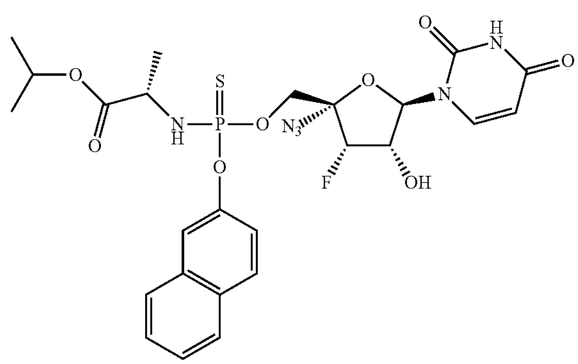 [SMILES: CC(C)OC(=O)[C@H](C)NP(=S)(OC[C@@]1(N=[N+]=[N-])O[C@@H](n2ccc(=O)[nH]c2=O)[C@H](O)[C@@H]1F)Oc1ccc2ccccc2c1] | 4'-Azido-3'-deoxy-3'-fluorouridine-5'-(O-2-naphthyl-N-(S)-1-(isopropoxycarbonyl)ethyl thiosphosphoramidate |
| I-4 | 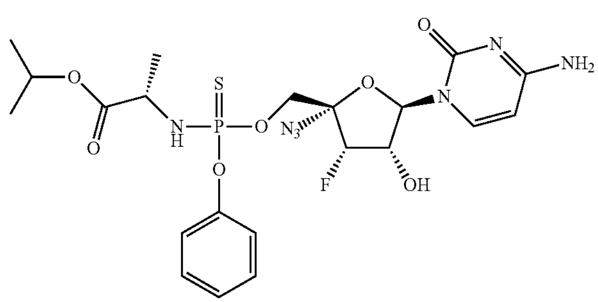 [SMILES: CC(C)OC(=O)[C@H](C)NP(=S)(OC[C@@]1(N=[N+]=[N-])O[C@@H](n2ccc(N)nc2=O)[C@H](O)[C@@H]1F)Oc1ccccc1] | 4'-Azido-3'-deoxy-3'-fluorocytidine-5'-(O-phenyl-N-(S)-1-(isopropoxycarbonyl)ethyl thiosphosphoramidate |
| I-5 | 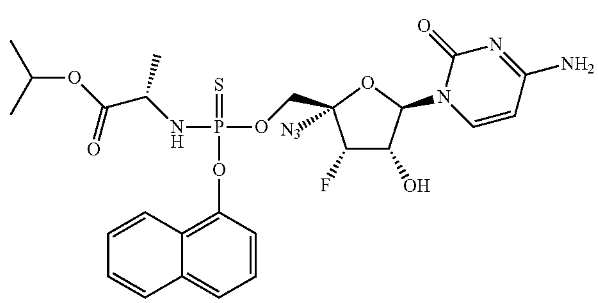 [SMILES: CC(C)OC(=O)[C@H](C)NP(=S)(OC[C@@]1(N=[N+]=[N-])O[C@@H](n2ccc(N)nc2=O)[C@H](O)[C@@H]1F)Oc1cccc2ccccc12] | 4'-Azido-3'-deoxy-3'-fluorocytidine-5'-(O-2-naphthyl-N-(S)-1-(isopropoxycarbonyl)ethyl thiosphosphoramidate |

TABLE 1-continued

| Compound Number | Structure | Name |
|---|---|---|
| I-6 | 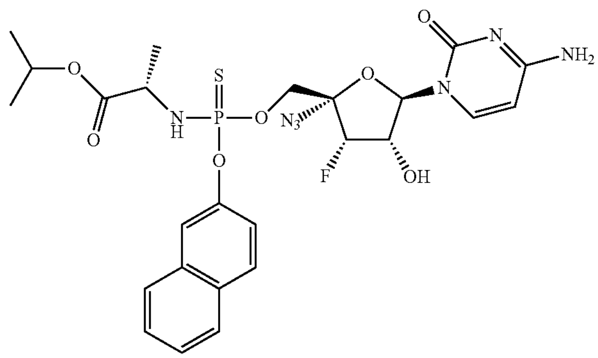 [SMILES: CC(C)OC(=O)[C@H](C)NP(=S)(OC[C@@]1(N=[N+]=[N-])O[C@@H](n2ccc(N)nc2=O)[C@H](O)[C@@H]1F)Oc1ccc2ccccc2c1] | 4'-Azido-3'-deoxy-3'-fluorocytidine-5'-(O-2-naphthyl-N-(S)-1-(isopropoxycarbonyl)ethyl thiosphosphoramidate |
| I-7 | 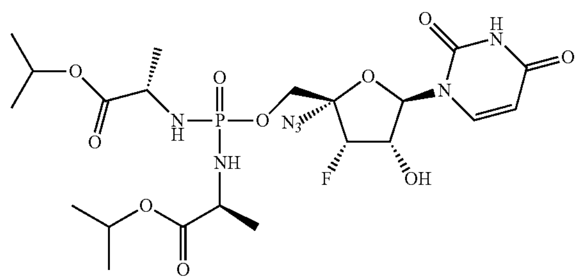 [SMILES: CC(C)OC(=O)[C@H](C)NP(=O)(N[C@@H](C)C(=O)OC(C)C)OC[C@@]1(N=[N+]=[N-])O[C@@H](n2ccc(=O)[nH]c2=O)[C@H](O)[C@@H]1F] | 4'-Azido-3'-deoxy-3'-fluorouridine-5'-{N,N'-bis[(S)-1-(isopropoxycarbonyl)ethyl] phosphorodiamidate |
| I-8 | 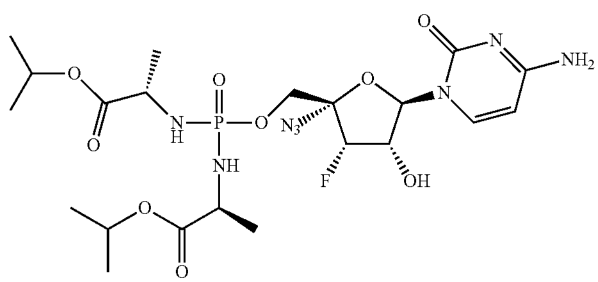 [SMILES: CC(C)OC(=O)[C@H](C)NP(=O)(N[C@@H](C)C(=O)OC(C)C)OC[C@@]1(N=[N+]=[N-])O[C@@H](n2ccc(N)nc2=O)[C@H](O)[C@@H]1F] | 4'-Azido-3'-deoxy-3'-fluorocytidine-5'-{N,N'-bis[(S)-1-(isopropoxycarbonyl)ethyl] phosphorodiamidate |
| I-9 | 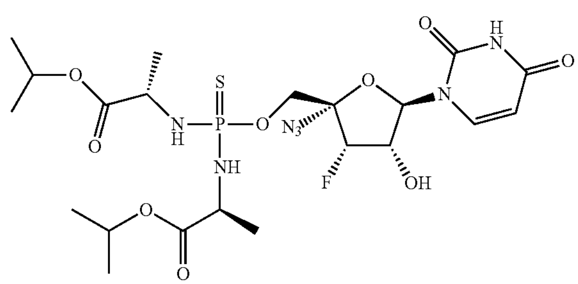 [SMILES: CC(C)OC(=O)[C@H](C)NP(=S)(N[C@@H](C)C(=O)OC(C)C)OC[C@@]1(N=[N+]=[N-])O[C@@H](n2ccc(=O)[nH]c2=O)[C@H](O)[C@@H]1F] | 4'-Azido-3'-deoxy-3'-fluorouridine-5'-{N,N'-bis[(S)-1-(isopropoxycarbonyl)ethyl] thiphosphorodiamidate |
| I-10 | 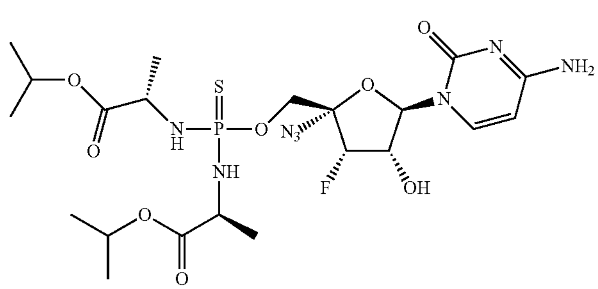 [SMILES: CC(C)OC(=O)[C@H](C)NP(=S)(N[C@@H](C)C(=O)OC(C)C)OC[C@@]1(N=[N+]=[N-])O[C@@H](n2ccc(N)nc2=O)[C@H](O)[C@@H]1F] | 4'-Azido-3'-deoxy-3'-fluorocytidine-5'-{N,N'-bis[(S)-1-(isopropoxycarbonyl)ethyl] thiphosphorodiamidate |

TABLE 1-continued

| Compound Number | Structure | Name |
|---|---|---|
| I-11 | 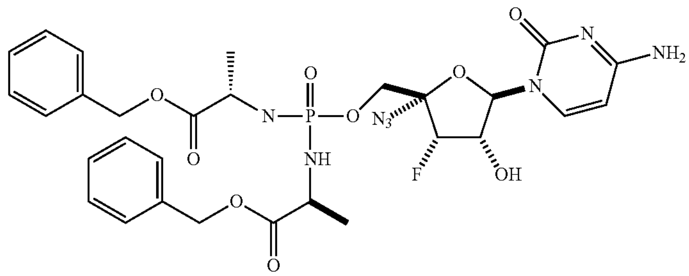 | 4'-Azido-3'-deoxy-3'-fluorocytidine-5'-{N,N'-bis[(S)-1-(benzyloxycarbonyl)ethyl]phosphorodiamidate |
| I-12 | 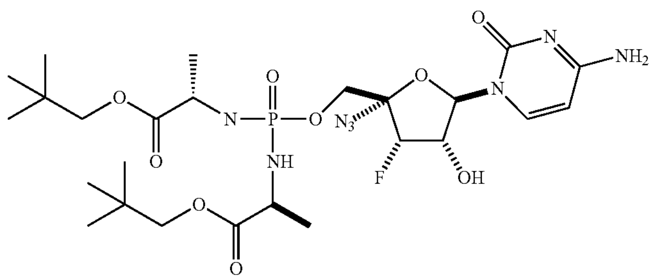 | 4'-Azido-3'-deoxy-3'-fluorocytidine-5'-{N,N'-bis[(S)-1-(2,2-dimethylpropyloxycarbonyl)ethyl]phosphorodiamidate |
| I-13 | 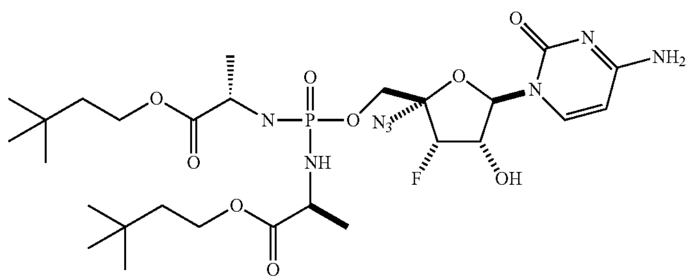 | 4'-Azido-3'-deoxy-3'-fluorocytidine-5'-{N,N'-bis[(S)-1-(3,3-dimethylpropyloxycarbonyl)ethyl]phosphorodiamidate |
| I-14 | 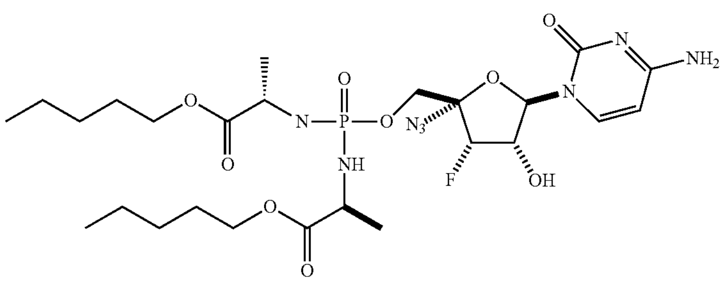 | 4'-Azido-3'-deoxy-3'-fluorocytidine-5'-{N,N'-bis[(S)-1-(pentyloxycarbonyl)ethyl]phosphorodiamidate |
| I-15 | 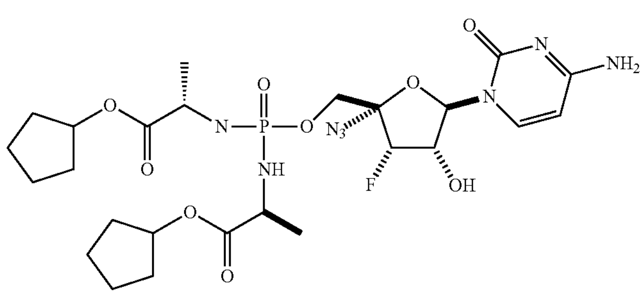 | 4'-Azido-3'-deoxy-3'-fluorocytidine-5'-{N,N'-bis[(S)-1-(cyclopentyloxycarbonyl)ethyl]phosphorodiamidate |

Synthesis

This application is related to publication Smith, David B.; Kalayanov, Genadiy; Sund, Christian; Winqvist, Anna; Maltseva, Tatiana; Leveque, Vincent J.-P.; Rajyaguru, Sonal; Le Pogam, Sophie; Najera, Isabel; Benkestock, Kurt; et al Journal of Medicinal Chemistry (2009), 52(9), 2971-2978.

General Schemes

The methods discussed above are described in more details below:

The commercially available nucleoside 3'-fluoro-3'-deoxyuridine (1) can also be prepared according to the procedures described by Gosselin, G. et al, *Collect. Czech. Chem. Com-* mun. (2006), Vol. 71, No. 7, 991-1010. Iodination followed by elimination of iodide under basic condition can lead to intermediate 3. Introduction of azido group at 4'α position in intermediate 3, followed by oxidative displacement of 5'-iodide with m-chloroperbenzoic acid in intermediate 4 to afford 5 can be accomplished according to the methods described by Smith, D. B. et al, *J. Med. Chem.* (2009), 52(9), 2971-2978. Deprotection of 5'm-chlorobenzoyl groups in intermediate 5 gives uridine intermediate 6 (Scheme 1).

Scheme 1.

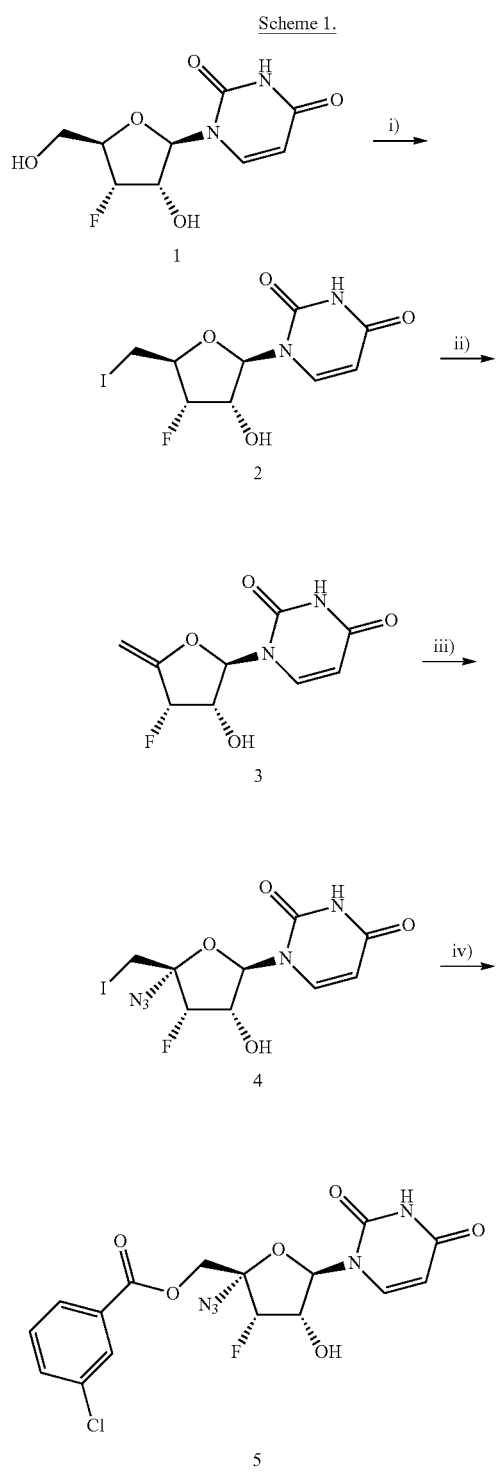

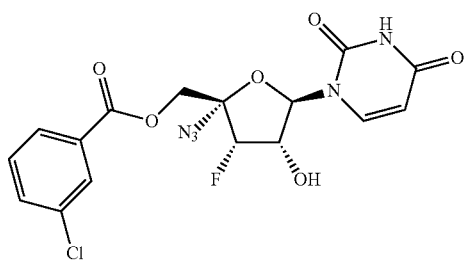

i) I₂, PPh₃, THF; ii) NaOMe, MeOH; iii) I₂, [Bn(Et)₃N]N₃, THF, MeCN; iv) mCPBA/mCBA, Bu₄NHSO₄, K₂HPO₄; v) NH₃, MeOH Cytidine intermediate 10 has been disclosed by Smith, D. B. et al in *J. Med. Chem.* (2009), 52(9), 2971-2978. Alternatively, 10 can also be efficiently prepared by the synthetic route outlined in Scheme 2.

Scheme 2.

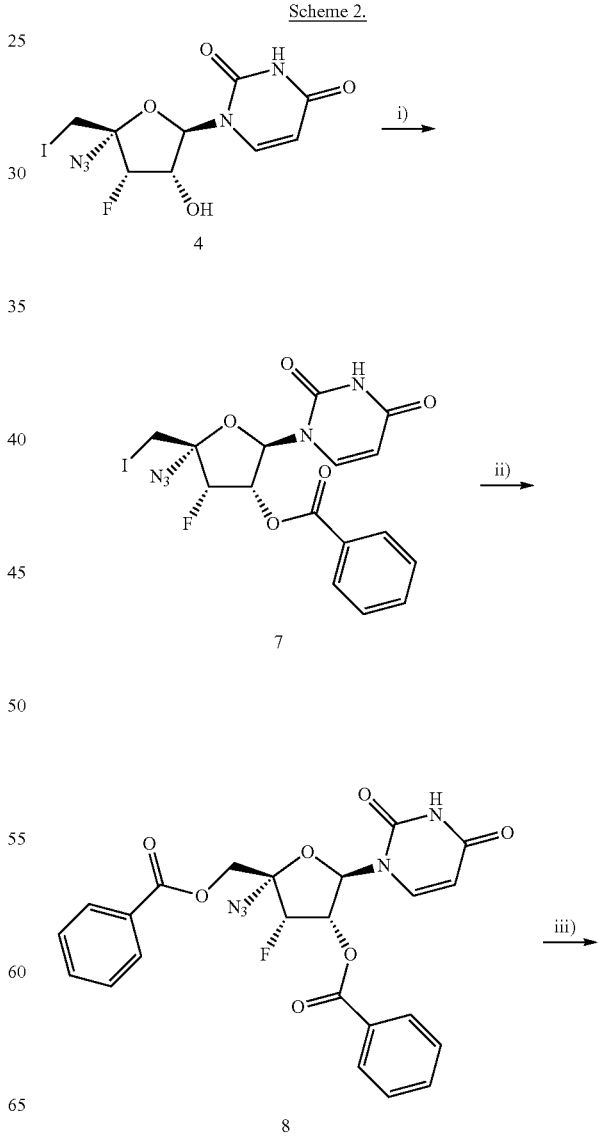

15

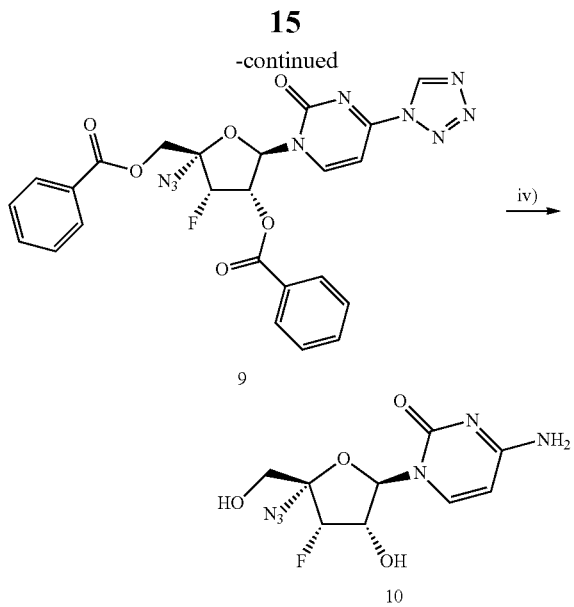

i) BzCl, DMAP, CH₂Cl₂; BzONa, DMSO; 1H-tetrazole, (4-Cl—PhO)P(O)Cl₂, Pyr; iv) NH₃, MeOH Phosphoramidate compounds of the present invention can be prepared by condensation of nucleoside 6 with a suitably substituted phosphoramidochloridothoic acid analogue, of type 11 in the presence of a strong base (Scheme 3). The coupled product 12 in Formula I are obtained as a mixture of two diastereomers initially under the coupling reaction and can be separated into their corresponding chiral enantiomers by chiral column, chiral HPLC, or chiral SFC chromatography.

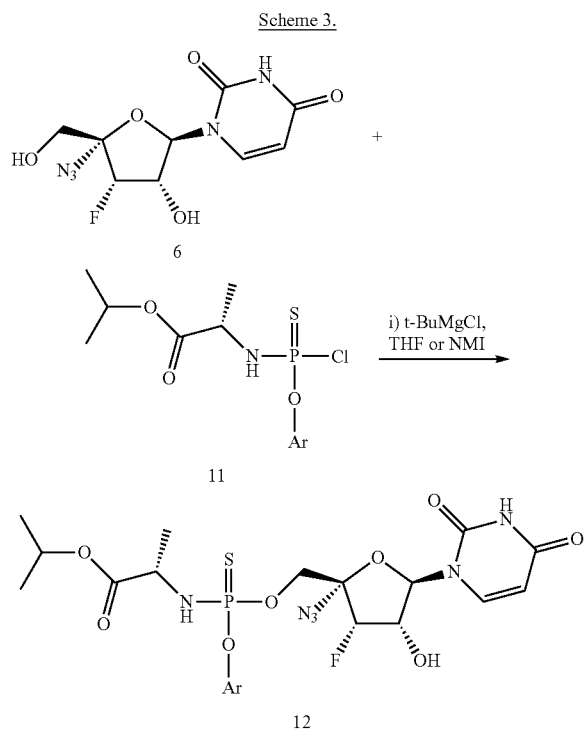

Phosphorodiamidate compounds of Formula I-7 to I-15 in the present invention can be prepared by condensation of nucleoside 6 with a suitably substituted phosphorodiamidic chloride, or phosphorodiamidothioic chloride, of type 13 (wherein the ester group can be substituted by a relevant alcohol) in the presence of a strong base (Scheme 4).

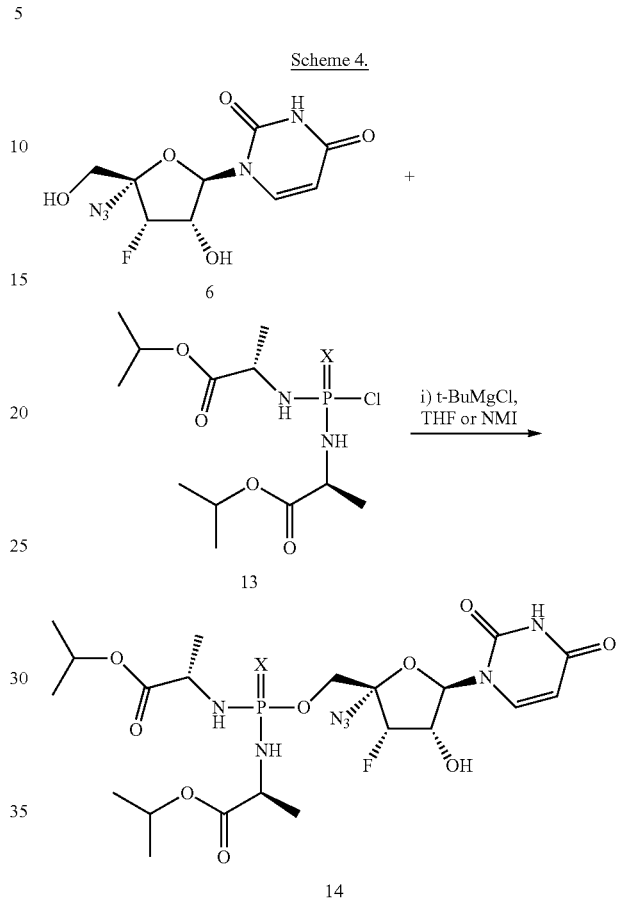

X = S or O

BIOLOGICAL EXAMPLES

HCV Replicon Assay

This assay measures the ability of the compounds of Formula I to inhibit HCV RNA replication, and therefore their potential utility for the treatment of HCV infections. The assay utilizes a reporter as a simple readout for intracellular HCV replicon RNA level. The *Renilla luciferase* gene is introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA is electroporated into human hepatoma Huh7 cells, and G418-resistant colonies are isolated and expanded. Stably selected cell line 2209-23 contains replicative HCV subgenomic RNA, and the activity of *Renilla luciferase* expressed by the replicon reflects its RNA level in the cells. The assay is carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, are cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium are added to the cells, which are then further incubated at 37° C. for three days. At the end of the incubation time, the cells in white plates are harvested and luciferase activity is measured by using the *R. luciferase* Assay system (Promega cat no. E2820). All the reagents described in the following paragraph are included in the manufacturer's kit, and the manufacturer's instructions are followed for preparations of the reagents. The cells are washed once with 100 µL of phosphate buffered saline (pH 7.0) (PBS) per well and lysed with 20 µl of 1× *R. luciferase* Assay lysis buffer prior to incubation at room temperature for 20 min. The plate is then inserted into the Centro LB 960 microplate luminometer (Berthold Technologies), and 100 µl of *R. luciferase* Assay buffer is injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) is used for the cytotoxicity assay. Ten microliter of WST-1 reagent is added to each well of the transparent plates including wells that contain media alone as blanks Cells are then incubated for 2 h at 37° C., and the OD value is measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

Dosage and Administration:

As shown in above Table the compounds of Formula I have the potential to be efficacious as antiviral drugs for the treatment of HCV infections in humans, or are metabolized to a compound that exhibit such activity.

In another embodiment of the invention, the active compound or its prodrug derivative or salt can be administered in combination with another antiviral agent, such as an anti-hepatitis agent, including those of Formula I. When the active compound or its derivative or salt are administered in combination with another antiviral agent the activity may be increased over the parent compound. This can easily be assessed by preparing the derivative and testing its anti-HCV activity according to the method described herein.

Administration of the active compound may range from continuous (intravenous drip) to several oral administrations per day (for example, Q.I.D) and may include oral, topical parenteral, intramuscular, intravenous, subcutaneous, transdermal (which may include a penetration enhancement agent), buccal and suppository administration, among other routes of administration.

The 4'-azido-3'-fluoro substituted nucleoside derivatives as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatine capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the 4'-substituted nucleoside derivatives, as well as their pharmaceutically useable salts, can be formulated with a therapeutically inert, inorganic or organic excipient for the production of tablets, coated tablets, dragées, hard and soft gelatine capsules, solutions, emulsions or suspensions.

The compounds of Formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragés, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatine capsules are, for example, vegetable oils, waxes, fats, semi-solid and liquid polyols.

Suitable excipients for injection solutions are, for example, water, saline, alcohols, polyols, glycerin or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to targeted site within the host organism or patient to maximize the intended effect of the compound.

Indications and Method of Treatment

The compounds of the invention and their isomeric forms and pharmaceutically acceptable salts thereof are useful in treating and preventing HCV infection.

The application provides a method for treating a Hepatitis C Virus (HCV) infection comprising administering to a patient in need thereof a therapeutically effective amount of a compound of any one of Formula I.

The application provides a method for inhibiting replication of HCV in a cell comprising administering a compound of any one of Formula I.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/40381; WO00/56331, WO02/04425;

WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021,927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a Hepatitis C Virus (HCV) infection comprising administering to a patient in need thereof a therapeutically effective amount of a compound of any one of Formula I.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

It will be understood that references herein to treatment extend to prophylaxis as well as to the treatment of existing conditions, and that the treatment of animals includes the treatment of humans as well as other mammals. Furthermore, treatment of an Hepatitis C Virus (HCV) infection, as used herein, also includes treatment or prophylaxis of a disease or a condition associated with or mediated by Hepatitis C Virus (HCV) infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

In compliance with 35 U.S.C. 102(c)(3), it is noted that Applicant, Ribo science LLC, F. Hoffmann-La Roche LTD, and Hoffmann-La Roche Inc. are hereby named as the parties to an Option, Transfer, and License Agreement which was entered into prior to the filing of the instant application and the claimed invention of the instant application was made as a result of activities undertaken within the scope of the agreement.

We claim:

1. A compound of Formula I:

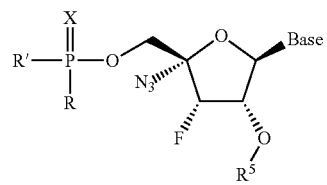

wherein:
R is O—$R^1$;
R' is $N(R^4)C(R^{2a})(R^{2b})C(=O)OR^3$;
  each $R^{1a}$ is independently H or lower alkyl;
  each $R^{1b}$ is independently —$OR^{1a}$ or —$N(R^{1a})_2$;
  each $R^{1c}$ is lower alkyl;
  each $R^{2a}$ and $R^{2b}$ are independently H, lower alkyl, —$(CH_2)_rN(R^{1a})_2$, lower hydroxyalkyl, —$CH_2SH$, —$(CH_2)S(O)_pMe$, —$(CH_2)_3NHC(=NH)NH_2$, (1H-indol-3-yl)methyl, (1H-indol-4-yl)methyl, —$(CH2)_mC(=O)R^{1b}$, aryl and aryl lower alkyl, wherein aryl may optionally be substituted with one or more hydroxy, lower alkyl, lower alkoxy, halo, nitro or cyano;
  m is 0 to 3;
  p is 0 to 2;
  r is 1 to 6;
  or $R^{2a}$ is H and $R^{2b}$ and $R^4$ together form $(CH_2)_n$;
  n is 4 or 5;
  $R^3$ is H, lower alkyl, lower haloalkyl, phenyl or phenyl lower alkyl;
  $R^4$ is H, lower alkyl, or $R^{2b}$ and $R^4$ together form $(CH_2)_3$;

$R^5$ is H, C(=O)$R^{1c}$, C(=O)$R^{1b}$, P(=O)(O$R^1$)(O$R^{1a}$), or P(=O)(O$R^1$)(N$R^4R^7$);

Base is uracil, cytosine, guanine, adenine, thymine, 7-deaza-7-fluoro adenosine or heterocycloalkyl, each of which may optionally substituted with one or more hydroxy, lower alkyl, lower alkoxy, halo, nitro or cyano; and X is S;

or a pharmacologically acceptable salt thereof.

2. The compound of claim 1, wherein $R^5$ is H, $R^4$ is H, $R^{2a}$ is H and $R^{2b}$ is methyl, and $R^1$ is optionally substituted naphthyl or phenyl.

3. The compound of claim 2, wherein $R^3$ is isopropyl.

4. The compound of claim 3, wherein Base is uracil or cytosine.

5. A compound of claim 1 selected from the group consisting of:
  4'-Azido-3'-deoxy-3'-fluorouridine-5'-(O-phenyl-N—(S)-1-(isopropoxycarbonyl)ethyl thiophosphoramidate;
  4'-Azido-3'-deoxy-3'-fluorouridine-5'-(O-1-naphthyl-N—(S)-1-(isopropoxycarbonyl)ethyl thiosphosphoramidate;
  4'-Azido-3'-deoxy-3'-fluorouridine-5'-(O-2-naphthyl-N—(S)-1-(isopropoxycarbonyl)ethyl thiosphosphoramidate;
  4'-Azido-3'-deoxy-3'-fluorocytidine-5'-(O-phenyl-N—(S)-1-(isopropoxycarbonyl)ethyl thiosphosphoramidate;
  4'-Azido-3'-deoxy-3'-fluorocytidine-5'-(O-2-naphthyl-N—(S)-1-(isopropoxycarbonyl)ethyl thiosphosphoramidate; and
  4'-Azido-3'-deoxy-3'-fluorocytidine-5'-(O-2-naphthyl-N—(S)-1-(isopropoxycarbonyl)ethyl thiosphosphoramidate.

6. A method for treating a Hepatitis C Virus (HCV) infection comprising administering to a patient in need thereof a therapeutically effective amount of a compound of claim 1.

7. A composition comprising the compound of claim 1, admixed with at least one carrier, diluent or excipient.

8. A compound of Formula I:

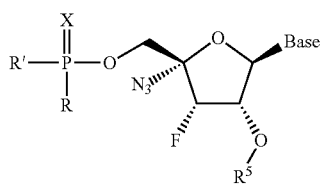

I wherein:
  R is N$R^4R^{1'}$;
  R' is N($R^4$)C($R^{2a}$)($R^{2b}$)C(=O)O$R^3$;
    $R^{1'}$ is —C($R^{2a}$)($R^{2b}$)C(=O)O$R^3$;
    $R^1$ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —CO$R^{1b}$, —SO$_2$($R^{1c}$), —NHSO$_2$($R^{1c}$), nitro or cyano;
    each $R^{1a}$ is independently H or lower alkyl;
    each $R^{1b}$ is independently —O$R^{1a}$ or —N($R^{1a}$)$_2$;
    each $R^{1c}$ is lower alkyl;
    each $R^{2a}$ and $R^{2b}$ are independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_3$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl may optionally be substituted with one or more hydroxy, lower alkyl, lower alkoxy, halo, nitro or cyano;
    m is 0 to 3;
    p is 0 to 2;
    r is 1 to 6;
    or $R^{2a}$ is H and $R^{2b}$ and $R^4$ together form (CH$_2$)$_n$;
    n is 4 or 5;
    $R^3$ is H, lower alkyl, lower haloalkyl, phenyl or phenyl lower alkyl;
    $R^4$ is H, lower alkyl, or $R^{2b}$ and $R^4$ together form (CH$_2$)$_3$;
  $R^5$ is H, C(=O)$R^{1c}$, C(=O)$R^{1b}$, P(=O)(O$R^1$)(O$R^{1a}$), or P(=O)(O$R^1$)(N$R^4R^7$);
  Base is uracil, cytosine, guanine, adenine, thymine, 7-deaza-7-fluoro adenosine or heterocycloalkyl, each of which may optionally substituted with one or more hydroxy, lower alkyl, lower alkoxy, halo, nitro or cyano; and
  X is S;
or a pharmacologically acceptable salt thereof.

9. The compound of claim 8, wherein $R^5$ is H, $R^4$ is H, $R^{2a}$ is H and $R^{2b}$ is methyl, and $R^1$ is optionally substituted naphthyl or phenyl.

10. The compound of claim 9, wherein $R^3$ is isopropyl.

11. The compound of claim 10, wherein Base is uracil or cytosine.

12. A compound of claim 8 selected from the group consisting of:
  4'-Azido-3'-deoxy-3'-fluorouridine-5'-{N,N'-bis[(S)-1-(isopropoxylcarbonyl)ethyl]thiphosphorodiamidate; and
  4'-Azido-3'-deoxy-3'-fluorocytidine-5'-{N,N'-bis[(S)-1-(benzyloxycarbonyl)ethyl]phosphorodiamidate.

13. A method for treating a Hepatitis C Virus (HCV) infection comprising administering to a patient in need thereof a therapeutically effective amount of a compound of claim 8.

14. A composition comprising the compound of claim 8, admixed with at least one carrier, diluent or excipient.

15. A compound of Formula I:

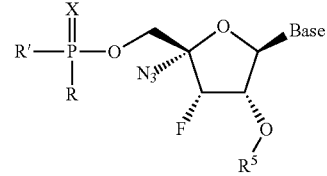

I wherein:
  R is N$R^4R^{1'}$;
  R' is N($R^4$)C($R^{2a}$)($R^{2b}$)C(=O)O$R^3$;
    $R^{1'}$ is —C($R^{2a}$)($R^{2b}$)C(=O)O$R^3$;
    each $R^{1a}$ is independently H or lower alkyl;
    each $R^{1b}$ is independently —O$R^{1a}$ or —N($R^{1a}$)$_2$;
    each $R^{1c}$ is lower alkyl;
    each $R^{2a}$ and $R^{2b}$ are independently H, lower alkyl, —(CH$_2$)$_r$N($R^{1a}$)$_2$, lower hydroxyalkyl, —CH$_2$SH, —(CH$_2$)S(O)$_p$Me, —(CH$_2$)$_3$NHC(=NH)NH$_2$, (1H-indol-3-yl)methyl, (1H-indol-4-yl)methyl, —(CH2)$_m$C(=O)$R^{1b}$, aryl and aryl lower alkyl, wherein aryl may optionally be substituted with one or more hydroxy, lower alkyl, lower alkoxy, halo, nitro or cyano;

m is 0 to 3;

p is 0 to 2;

r is 1 to 6;

or $R^{2a}$ is H and $R^{2b}$ and $R^4$ together form $(CH_2)_n$;

n is 4 or 5;

$R^3$ is H, lower alkyl, lower haloalkyl, phenyl or phenyl lower alkyl;

$R^4$ is H, lower alkyl, or $R^{2b}$ and $R^4$ together form $(CH_2)_3$;

$R^5$ is H, C(=O)$R^{1c}$, C(=O)$R^{1b}$, P(=O)(O$R^1$)(O$R^{1a}$), or P(=O)(O$R^1$)(N$R^4R^7$);

Base is uracil, cytosine, guanine, adenine, thymine, 7-deaza-7-fluoro adenosine or heterocycloalkyl, each of which may optionally substituted with one or more hydroxy, lower alkyl, lower alkoxy, halo, nitro or cyano; and X is O;

or a pharmacologically acceptable salt thereof.

16. The compound of claim 15, wherein $R^5$ is H, $R^4$ is H, $R^{2a}$ is H and $R^{2b}$ is methyl, $R^1$ is optionally substituted naphthyl or phenyl, and Base is uracil or cytosine.

17. The compound of claim 16, wherein $R^3$ is isopropyl.

18. A compound of claim 15 selected from the group consisting of:

4'-Azido-3'-deoxy-3'-fluorouridine-5'-{N,N'-bis[(S)-1-(isopropoxylcarbonyl)ethyl]phosphorodiamidate;

4'-Azido-3'-deoxy-3'-fluorocytidine-5'-{N,N'-bis[(S)-1-(benzyloxycarbonyl)ethyl]phosphorodiamidate;

4'-Azido-3'-deoxy-3'-fluorocytidine-5'-{N,N'-bis[(S)-1-(2,2-dimethylpropyloxylcarbonyl)ethyl]phosphorodiamidate;

4'-Azido-3'-deoxy-3'-fluorocytidine-5'-{N,N'-bis[(S)-1-(3,3-dimethylbutyloxylcarbonyl)ethyl]phosphorodiamidate;

4'-Azido-3'-deoxy-3'-fluorocytidine-5'-{N,N'-bis[(S)-1-(pentyloxylcarbonyl)ethyl]phosphorodiamidate; and 4'-Azido-3'-deoxy-3'-fluorocytidine-5'-{N,N'-bis[(S)-1-(cyclopentyloxylcarbonyl)ethyl]phosphorodiamidate.

19. A method for treating a Hepatitis C Virus (HCV) infection comprising administering to a patient in need thereof a therapeutically effective amount of a compound of claim 15.

20. A composition comprising the compound of claim 15, admixed with at least one carrier, diluent or excipient.

* * * * *